(12) United States Patent
Keene

(10) Patent No.: US 7,481,820 B1
(45) Date of Patent: Jan. 27, 2009

(54) TISSUE GRAFT SUPPORT APPARATUS

(76) Inventor: Sharon Keene, c/o Physician's Hair Institute, 310 N. Wilmot, Suite 304, Tucson, AZ (US) 85711

( * ) Notice: Subject to any disclaimer, the term of this patent is extended or adjusted under 35 U.S.C. 154(b) by 816 days.

(21) Appl. No.: 10/852,250

(22) Filed: May 24, 2004

Related U.S. Application Data

(60) Provisional application No. 60/473,030, filed on May 23, 2003.

(51) Int. Cl.
*A61B 17/34* (2006.01)
(52) U.S. Cl. ..................................... 606/187
(58) Field of Classification Search ................ 606/187, 606/133, 184; 428/131, 132; 224/148, 218, 224/222; 433/163, 49; 223/106, 107; 422/99; 206/229, 230, 361, 362.3
See application file for complete search history.

(56) References Cited

U.S. PATENT DOCUMENTS

| 5,222,643 | A | * | 6/1993 | Platt | 224/218 |
| 5,562,732 | A | | 10/1996 | Eisenberg | 623/15 |
| 5,584,851 | A | | 12/1996 | Banuchi | 606/187 |
| 5,611,811 | A | | 3/1997 | Goldberg | 606/187 |
| 5,817,120 | A | | 10/1998 | Rassman | 606/187 |
| 5,868,758 | A | | 2/1999 | Markman | 606/133 |
| 5,873,888 | A | | 2/1999 | Costanzo | 606/187 |
| 5,899,916 | A | | 5/1999 | Casparian | 606/187 |
| 5,958,341 | A | * | 9/1999 | Chu | 422/99 |
| 5,989,279 | A | | 11/1999 | Rassman | 606/187 |
| 6,120,521 | A | | 9/2000 | Casparian | 606/187 |
| 6,270,511 | B1 | | 8/2001 | Markman | 606/187 |
| 6,328,159 | B1 | * | 12/2001 | Discko, Jr. | 206/229 |

* cited by examiner

*Primary Examiner*—Kevin T Truong
(74) *Attorney, Agent, or Firm*—Hayes Soloway P.C.

(57) ABSTRACT

A tissue graft holder comprising a tray having a plurality of compartments for supporting tissue grafts and a hydrating solution, a channel connecting each compartment to an edge of the tray. The tray is rotatably mounted to a support which in turn is adapted for attachment to an appendage of a user. A dissecting cutting board to accommodate the graft trays and maintain tissue hydration during graft dissection.

15 Claims, 7 Drawing Sheets

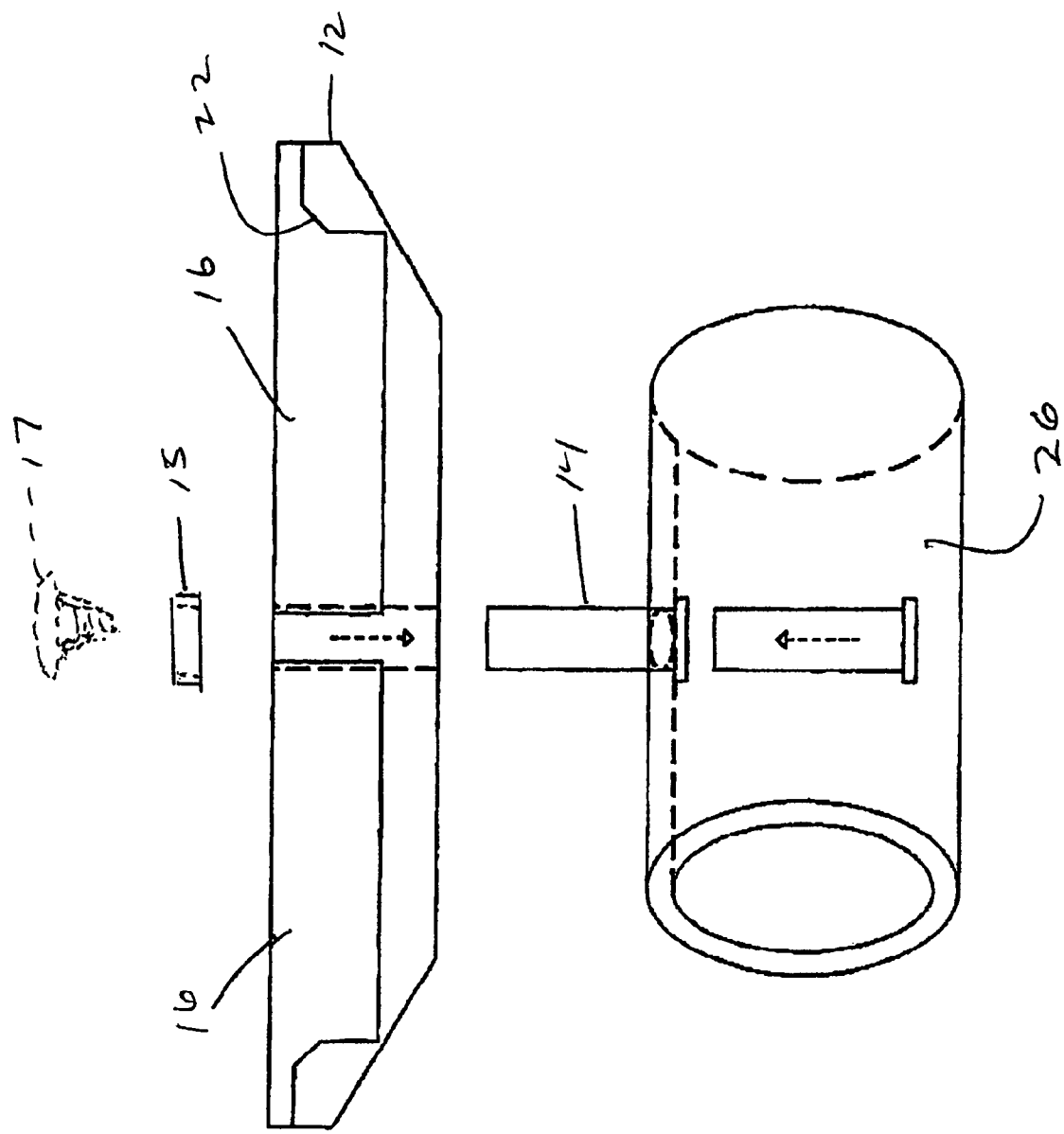

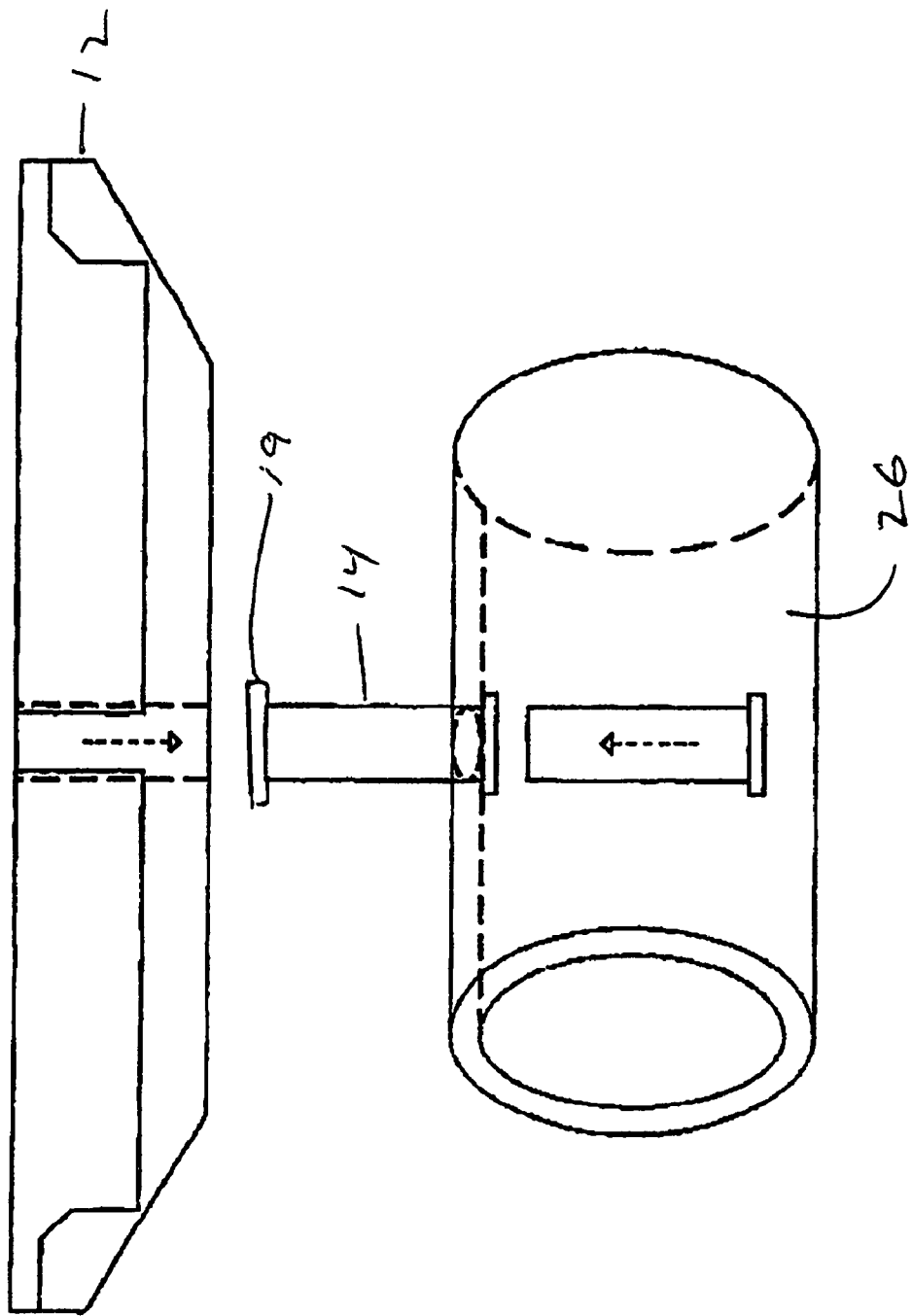

TISSUE GRAFT SUPPORT APPARATUS

CROSS REFERENCE TO RELATED APPLICATION

This application claims priority under 35 USC 119 from U.S. Provisional Patent Application Ser. No. 60/473,030, filed May 23, 2003.

FIELD OF THE INVENTION

This invention relates generally to the field of devices for use in dermatologic surgery and cosmetology. The invention has particular utility for use in connection with hair transplantation procedures and will be described in connection with such utility, although other utilities are contemplated.

BACKGROUND OF THE INVENTION AND DESCRIPTION OF PRIOR ART

State of the art surgery for cosmetic hair transplantation involves redistributing permanent hair follicles from the back and sides of the head, to areas of hair loss. The most cosmetic method involves placing small bundles of hair—as they naturally occur—in small, closely approximated incisions on the scalp. Experience has shown the scalp has excellent blood supply and can support the transfer of at least 2000 of these bundles into 2000 small recipient sites on the scalp in one sitting. The bundled follicles are called "follicular unit grafts", and the large numbers of grafts placed in a single surgery are referred to as megasessions. Each graft is carefully dissected from surrounding tissue, into a graft containing from 1-4 hairs, as it naturally occurred.

The one physical insult that can most impact graft survival is desiccation. Grafts are typically stored in a Petri dish surrounded in saline solution, prior to graft placement. Because of the risk of desiccation, most of the grafts are left in the Petri dish until just prior to placement. This usually involves transferring the graft from the Petri dish to the surgeon or the surgeon's assistant's finger, in preparation for placement into the scalp recipient site for transplantation. As will be appreciated, this is tedious and time consuming.

Various instruments have been developed for facilitating graft placement and are available commercially and/or described in the patent literature. They include the Choi implanter which is a spring loaded needle nose graft injector device. With a Choi implanter a single graft is threaded into the needle nose and injected into the incision. Thus, it is time consuming and expensive. One person must load the device prior to handing it off to the operating person in order to keep the flow smooth. An individual skilled operator can easily place grafts more quickly without the device, provided they do not have to turn and load grafts onto the finger from a Petri dish, and do repetitive unnecessary movements away from the patient's scalp.

Another hair transplant instrument is described in U.S. Pat. No. 5,584,851 to Banuchi. The Banuchi instrument does not actually implant grafts into the scalp. Rather, it is a shallow, rectangular tray, which narrows to a point in the front. The tray has separate ridges that form shallow troughs for the purpose of aligning grafts one above another. The tray does not allow for significant or immersible hydration of the grafts, although there is some. The operator is meant to pull the graft down through the shallow canal into the tip, and then into the incision. The tray has a limited graft holding capacity. It has a shallow design, and limited width, as this tray is intended to be hand held by the operator using the index finger and thumb. The design limits the operator's ability to utilize the hand which holds the Banuchi implanter, leaving it unavailable to perform any other function while doing this task. Also, should the operator loosen their grip or the tray slip, grafts are at risk for spillage.

U.S. Pat. Nos. 5,989,279 and 5,817,120 to Rassman describe a implantation device having a shallow tray with individual narrow channels each to hold a single graft. A spring-loaded mechanism advances the tray, while automatically unloading the graft into a pointed tip, which inserts the grafts into the recipient sites (either incisions or holes). This device reportedly is prone to jamming during use, has a limited capacity to hold grafts, has no capacity to keep grafts immersed in hydrating solution, and also is hand held.

U.S. Pat. No. 5,562,732 to Eisenberg describes a hair graft support tray system for mounting on the finger of a user. The Eisenberg hair graft support tray system includes a slidably mounted tray fixed to a tray support which includes a finger ring for retaining the tray on a finger of the user. The tray includes a plurality of grooves having drainage holes located in the grooves. Accordingly to Eisenberg, the tray is filled with micro- or mini-grafts and placed in storage in a saline solution until use. However, once the Eisenberg tray is removed from storage for use, there is nothing to retain the saline around the grafts, and the grafts are prone to dehydration. The drainage holes in the tray actually prevent immersible hydration from occurring and subject grafts to potential dessication during the insertion process of placement. Also, many users find the ring retention design of the Eisenberg support tray to be somewhat uncomfortable.

Yet other designs are described in U.S. Pat. No. 5,611,811 to Goldberg, U.S. Pat. Nos. 6,270,511 and 5,868,758 to Markman, U.S. Pat. No. 5,873,888 to Costango, U.S. Pat. Nos. 5,899,916 and 6,120,521 to Casparian.

SUMMARY OF THE INVENTION

The present invention overcomes the aforesaid and other problems to the prior art by providing a system for use in transplant surgery comprising a compartmentalized reservoir for holding a plurality of grafts. The nature of the graft reservoir provides complete immersion of grafts in a discrete volume of hydrating solution, unlike current Petri dishes where grafts are placed in piles but cannot be immersed without causing floating and mixing of graft sizes. There is evidence to support immersion as superior to simply allowing the grafts to sit in a damp Petri dish. An open ended channel or spout extends from each of the reservoir compartments to an edge of the device for permitting the surgeon to separate and remove a follicular unit which may comprise one or a plurality of individual hair grafts. In a preferred embodiment of the invention, the hair transplant support is designed to fit over the finger, wrist or hand of the surgeon and held there by means of a suitably sized plastic or other bio-compatible tubing, either intact so it may slip over the finger like a tube, or sliced open so it can be pressed or compressed over the finger like a semi-circular clasp, alternatively it may be wound around the appendage with a malleable or bendable material such as light weight aluminum. Alternatively it may be secured on the wrist or hand with an adjustable strap or similar type of tubelike attachment adjusted for diameter of the finger, wrist or hand. Preferably the reservoir is designed to rotate so that the several compartments may be repositioned for use, exposing a selected compartment with a certain size graft to the spout nearest the scalp incision, for example single hair grafts for the front hairline. The rotational apparatus of the device is part of the attachment, as the central pin or pole connects the attachment to the reservoir through a middle opening. The reservoir preferably is rotatably secured to the pin by friction, or the reservoir may be rotatably secured to the pin, by use e.g., of an O-ring or C-ring on top of the pin, or a malleable cap fitted over the top end pin. Other configurations to secure the pin to the attachment include a screw or nut. Or, the top of the pin may be flared. Any configuration that allows controlled rotation of the reservoir, while maintaining the reservoir on the pin may be used.

The compartments are designed to hold saline in which follicular unit grafts are placed. This permits the surgeon to separate various size grafts while maintaining hydration. In use, an individual graft, which may comprise one or several hair follicles is separated or pulled from a compartment to an associated channel or spout where the graft may then be gripped with forceps, removed and transplanted immediately to the patients recipient scalp area. Another feature of the compartments is the efficient use of space eliminating waste and compacting the storage area of the grafts. Unlike Petri dishes where hydration solution covers a relatively large area in comparison to the grafts, and requires several milliliters of fluid, each compartment requires only a small amount of fluid to maintain graft immersion for hundreds of hairs. This latter feature is particular advantageous in that it permits efficient use of more expensive solutions which recently have been developed which improve graft survival.

DESCRIPTION OF THE DRAWINGS

The foregoing and other features and advantages of the present invention will be seen from the following detailed description, wherein:

FIG. 3 is an exploded view of portions of the hair graft support instrument of FIG. 1;

FIG. 3A is a view similar to FIG. 3, of an alternative hair graft support instrument made in accordance with the present invention;

DETAILED DESCRIPTION OF PREFERRED EMBODIMENTS

Figure 1:
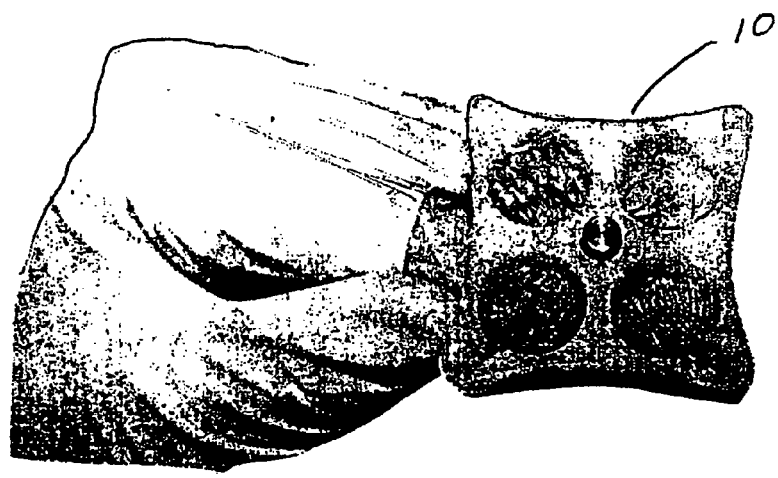
FIG. 1 is a side perspective view of a tissue graft holder in accordance with one embodiment of the present invention, in place on a surgeon's hand.
Figure 2:
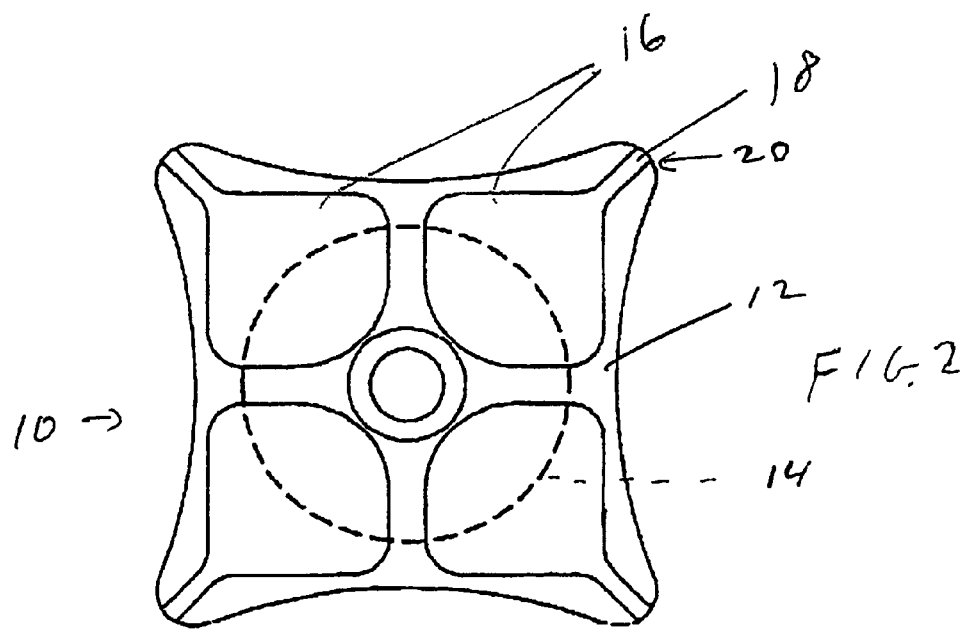
FIG. 2 is a top plan view of the hair graft support instrument of FIG. 1.
Figure 4:
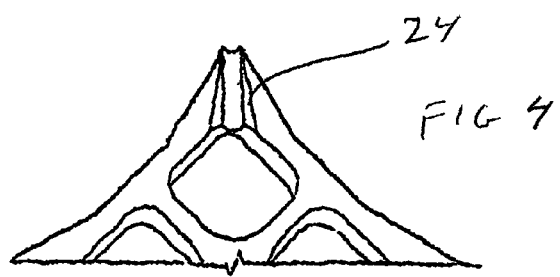
FIG. 4 is a perspective view of a portion of the hair graft support instrument of FIG. 1.
Figure 5:
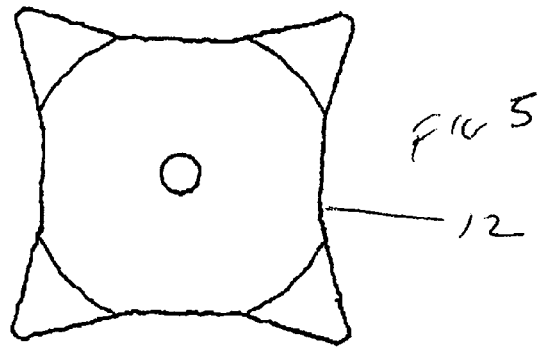
FIG. 5 is a bottom view of the hair graft support tray portion of FIG. 1.

Referring first to FIGS. 1-5, there is provided a hair graft holder 10 comprising a tray 12 rotatably mounted on a base or pin 14. Tray 12 is rotatably mounted on base 14 and held in place by friction, or by use of e.g., an O-ring or C-ring or a malleable cap or nut shown generically at 15 fitted over the top end of the pin. Alternatively, the tray 12 may be rotatably mounted to the pin by a screw shown in phantom at 17 in FIG. 3, or the top of the pin may be flared, e.g., as shown at 19 in FIG. 3A. Preferably tray 12 is removable from pin 14. A tray 12 and pin 14 preferably are formed of a bio-compatible autoclavable or disposable material such as Teflon, polyethylene, or Delrin. Tray 12 is generally a square in overall plan and includes a plurality of compartments 16. An open channel or spout 18 communicates with each compartment 16 and extends to an outside corner 20 of the tray 12. As best seen in FIGS. 3 and 4, channels 18 are quite shallow compared to compartments 16 and are connected to compartment 16 by a sloping bottom wall 22. As will become clear from the description following, channels 18 are made shallow compared to compartment 16 so that saline will not easily drain from compartments 16. The side walls 24 of channels 18 preferably are tapered outwardly.

A removable adjustable hand or finger mount 26 which may be in the form of short stub tubing or an adjustable strap is provided cooperating with base 14 so that the holder 10 may be worn on a finger, hand or wrist of the user.

Compartments 16 typically are 0.8-1.0 cm deep which is sufficient to hold graft material and to maintain hydration of the grafts. Depending on the size of the compartments, several hundred follicles could be held in each compartment.

Figure 6:
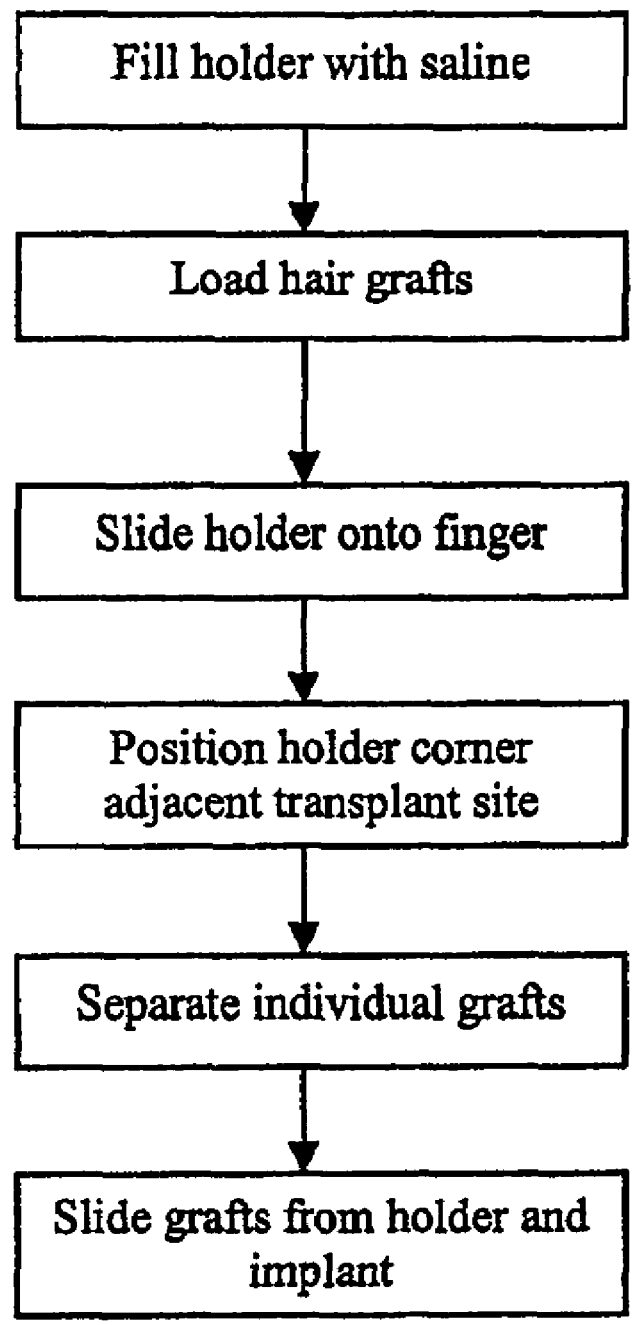
FIG. 6 is a flow chart depicting steps in a hair transplantation procedure using the hair graft support instrument in accordance with the present invention.

FIG. 6 shows a flow chart which explains the hair transportation procedure using the hair graft holder of the present invention. Referring to FIG. 6, hair grafts are harvested and placed into the compartments 16 previously filled with saline. The hair graft holder is then slid onto the finger or hand of the operator, and the holder is held with corner 20 near the scalp of the patient providing ready access to well hydrated grafts. The surgeon may then separate individual grafts containing, typically, 1-4 hairs, slide the separated hairs from the compartment 16 into channel 18 where the separated hairs may then be removed from the holder and implanted. The whole operation, i.e., from separating a graft to implantation may take a matter of seconds, during which there is no chance for the graft to dehydrate.

The above described hair graft holder provides significant advantages over prior art hair graft support trays. For one, it is designed to be mounted on the finger, hand or wrist of the user. Thus, it does not require constant finger grip which can be fatiguing, and also permits the operator additional use of the graft holding hand. Also, the soft plastic tubing or adjustable strap is more comfortable than hard rings such as used in the Eisenberg tray. Hundreds of grafts may be stored in the compartments, which saves hours in the hair transplant process while decreasing graft dehydration and improving graft survival. Moreover, by terminating the spouts or channels adjacent a corner of the tray, the tray may be used to closely position the graft to the target location, essentially serving as a finger of the surgeon or assistant. And, by providing a plurality of compartments, as the follicles are depleted from one compartment, it is a simple matter to rotate the tray to permit access to another compartment and fresh hydrated hair follicles. It is not necessary for the surgeon to turn away from the operative field in order to "load up" more grafts. Another feature and advantage of the present invention is that the several compartments permit the surgeon to separate the grafts according to size for ease of placement.

Figure 7:
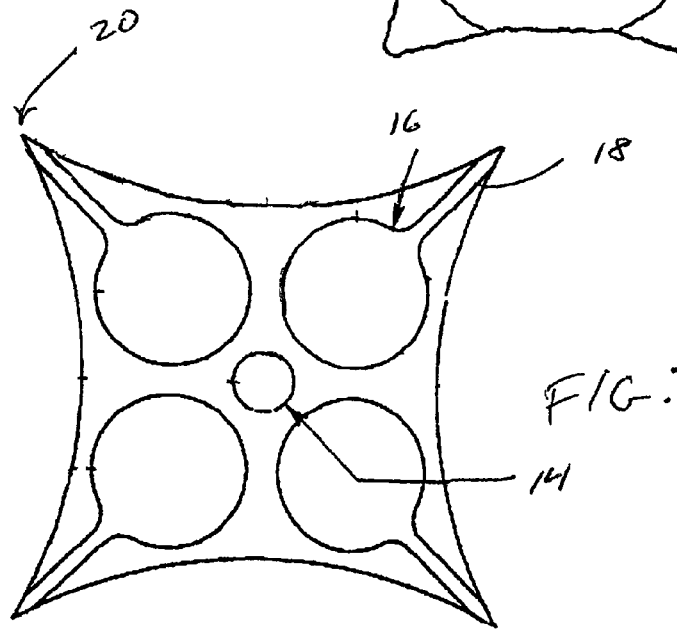
FIG. 7 is a top plan view of an alternative hair graft support instrument in accordance with the present invention.

The invention is susceptible to modification. For example, as shown in FIG. 7, the compartments may be round in plan rather than square. Also, the tray can have other shapes including triangular, or five or more sides, with the corresponding number of compartments and channels or spouts. Alternatively, the tray can be round in plan, with a plurality of spouts extending radially between the compartments to beyond the tray periphery.

Figure 8:
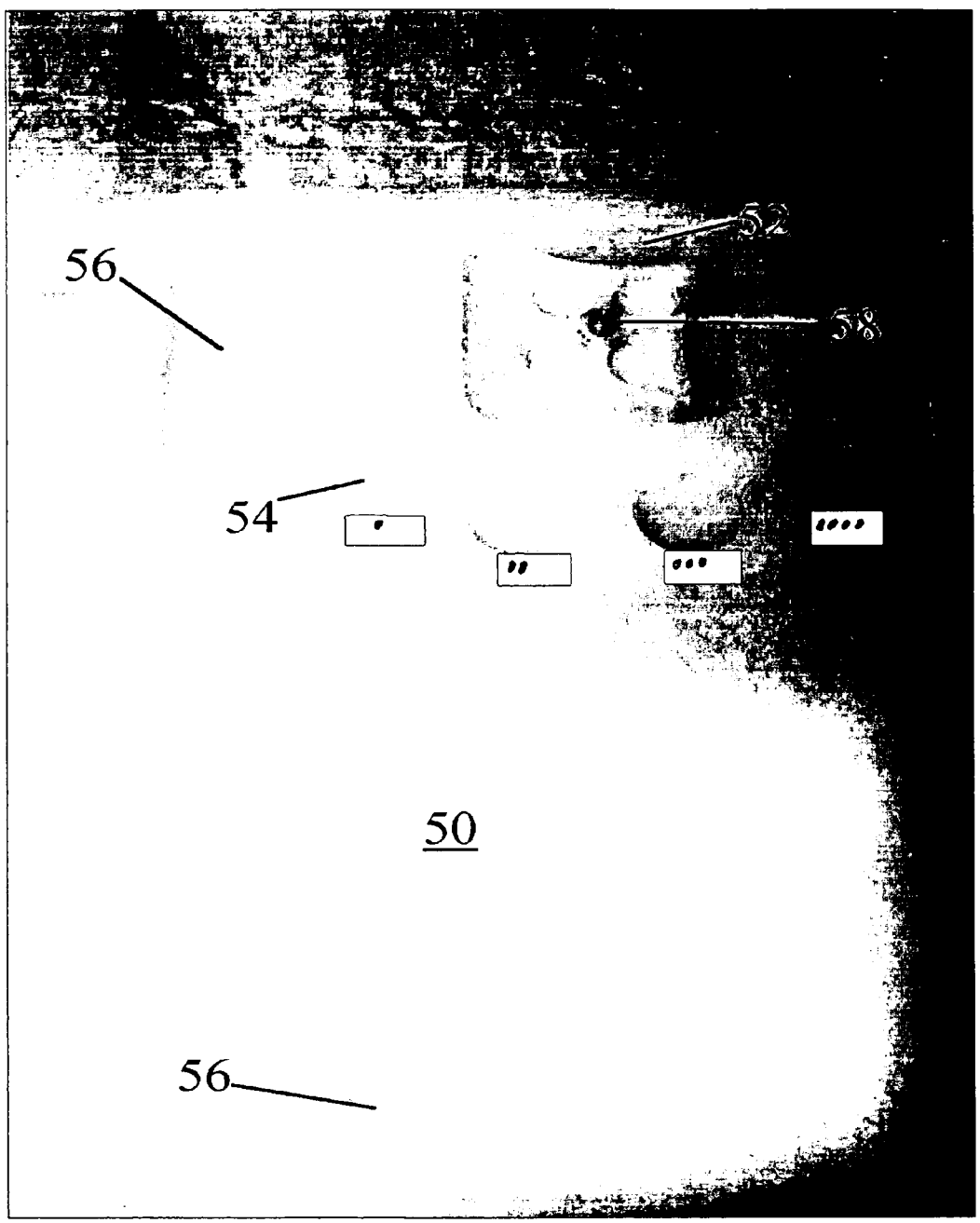
FIGS. 8 and 9 illustrate cutting boards useful in a preferred embodiment of the invention.

Referring to FIG. 8, there is shown a cutting board 50 made in accordance with a one embodiment of the invention. Cutting board 50 comprises a generally planar rigid board formed of a bio-compatible autoclavable or disposable material such as Teflon, polyethylene or Delrin. Alternatively, board 50 may be formed of stainless steel. However, making the tray of a translucent material is preferred since it permits illumination from below. Board 50 includes a first compartment 52 sized to hold tray 12 and a plurality of smaller compartments 54 for holding graft material while it is being dissected. If desired, indicia may be applied adjacent compartments 54 corresponding to indicia applied to adjacent compartments 16 on tray 12.

To facilitate handling of the tray, one or more finger grips 56 are providing adjacent one or more edges of the tray, and extending through the tray. Also, a pin 58 is provided in the center of compartment 52 for rotatably holding tray 12.

In use, the compartments 52 and 54 are partly filled with saline or other fluid for hydrating the grafts. The grafts may then be harvested, dissected, sorted by size and stored temporarily in compartments 54 prior to loading into the compartments in tray 12. The rotational mounting of tray 12 permits the user to rotate tray 12 to align a selected compartment 16 with a selected compartment 54 on the cutting board.

Figure 9:
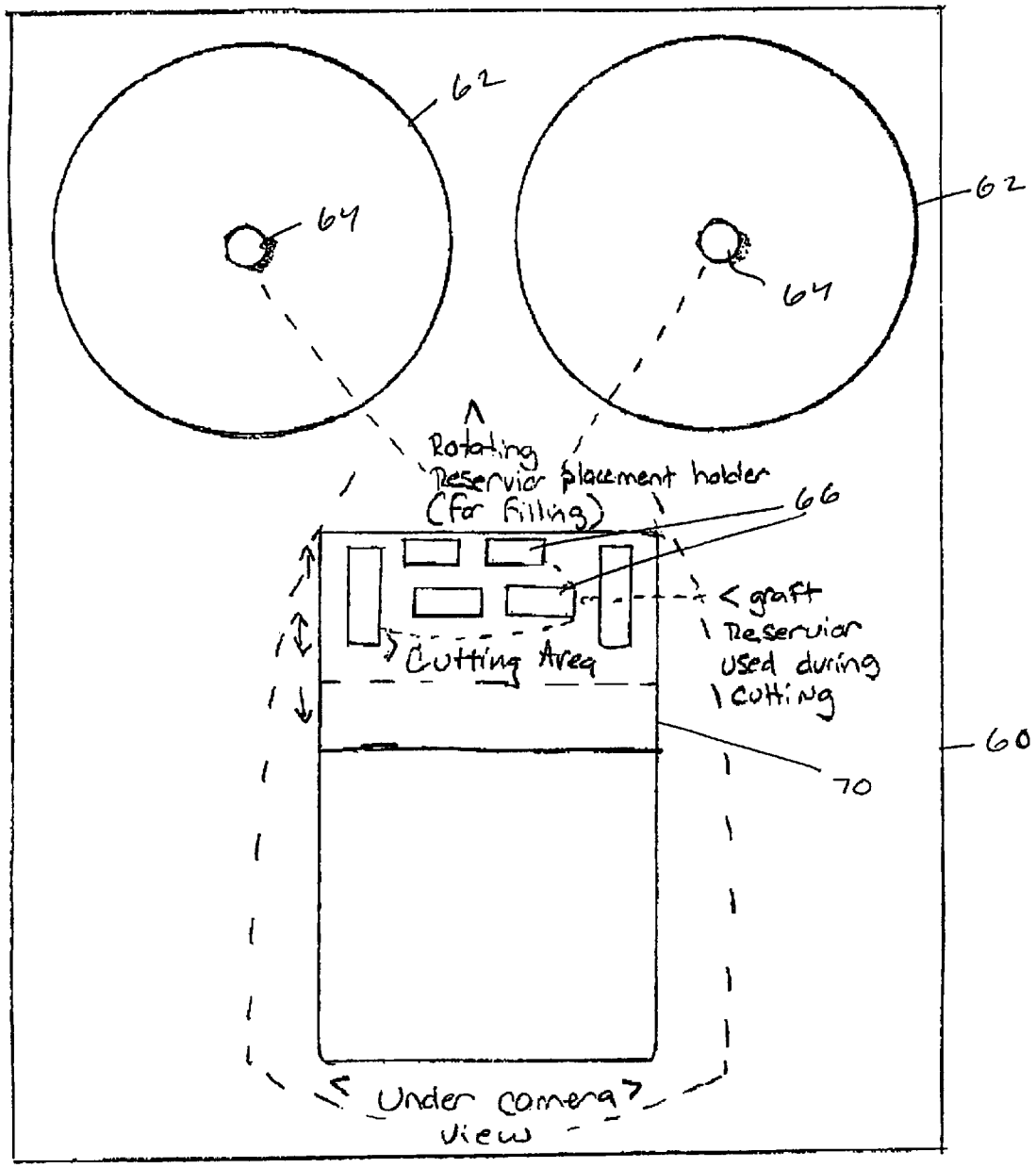

Another and preferred embodiment of cutting board 60 is shown in FIG. 9. Cutting board 60 includes two compartments 62 for rotatably holding two hair graft trays. As before pins 64 are provided so that the hair graft trays may be rotated. Also as before, the cutting board includes a plurality of smaller compartments 66 in which grafts may be cut and stored prior to loading into a hair graft tray. Compartments 66 are formed in an area 70 which itself is slightly recessed from the main surface of the board so that the cutting area may also be flooded with saline or other fluid for hydrating the grafts.

Preferably, hair graft holder 10 and cutting board 50 or 60 of the present invention are used together. It will be appreciated however that the hair graft holder 10 of the present invention and the cutting board 50 or 60 also may be used separately.

While the invention has been described in connection with hair transplant surgery, the invention may also be advantageously used with other surgical and non-surgical procedures. The invention may also be used in other fields such as dyes for tattoos, paints for artists, crèmes and make-up for cosmetologists and aestheticians. The tray also may be sized to fit on the hand or wrist.

The invention has been described with respect to the particular illustrative embodiments. It is to be understood however that the invention is not limited to the above-described embodiments and modifications thereto, and that various changes and modifications may be made without departing from the spirit and scope of the appended claims.

The invention claimed is:

1. A tissue graft holder comprising, in combination
a tray having a plurality of compartments for supporting tissue grafts and for holding a hydrating solution;
a channel connecting each compartment to an edge of the tray; and
a tray support for attachment to an appendage of a user,
wherein said channels are shallower than said compartments and terminate as spouts extending to an edge of said tray.

2. The tissue graft holder of claim 1, wherein said tray is rotatably mounted to said tray support.

3. The tissue graft holder of claim 1, wherein said tray support comprises stub tubing sized for a finger, hand or wrist of a user.

4. The tissue graft holder of claim 1, wherein said tray support comprises an adjustable strap sized for a finger, hand or wrist of a user.

5. The tissue graft holder of claim 4, wherein said adjustable strap includes an adjustable closure.

6. The tissue graft holder of claim 2, wherein the tray is held rotatably mounted to the support by a screw or nut, an O-ring or C-ring, or a cap.

7. The tissue graft holder of claim 2, wherein the tray is held rotatably mounted to the support by friction fit or the support is flared.

8. The tissue graft holder of claim 1, wherein said channels terminate at corners of said tray.

9. The tissue graft holder of claim 1, wherein said spouts are shallower than said compartments.

10. The tissue graft holder of claim 9, wherein said channels include a sloped transition portion running to said compartments.

11. The tissue graft holder of claim 1, wherein said holder is substantially square in plan and said channels run to corners of said holder.

12. The tissue graft holder of claim 1, wherein each of said compartments has indicia associated therewith.

13. A method for transplanting hair grafts which comprises loading a tissue graft holder as claimed in claim 1 with a plurality of hair grafts in a hydrating solution;
separating follicular unit grafts from said plurality; and
positioning said separated follicular unit adjacent a transplantation site, and planting the separated follicular unit in a transplantation site.

14. The method of claim 13, and including the step at least partly filling the compartments of the tissue graft holder with a hydrating solution prior to loading said hair grafts therein.

15. The method of claim 13, wherein said hydrating solution comprises saline.

* * * * *